United States Patent
Vohra et al.

(10) Patent No.: US 7,875,039 B2
(45) Date of Patent: Jan. 25, 2011

(54) SUPPORT ASSEMBLY FOR A TRACKING ASSEMBLY AND MOUNTED TRANSRECTAL ULTRASOUND PROBE

(75) Inventors: Amit Vohra, Grass Valley, CA (US); Jasjit S. Suri, Roseville, CA (US)

(73) Assignee: Eigen, Inc., Grass Valley, CA (US)

( * ) Notice: Subject to any disclaimer, the term of this patent is extended or adjusted under 35 U.S.C. 154(b) by 367 days.

(21) Appl. No.: 12/207,708

(22) Filed: Sep. 10, 2008

(65) Prior Publication Data

US 2009/0326554 A1 Dec. 31, 2009

Related U.S. Application Data (60) Provisional application No. 61/078,164, filed on Jul. 3, 2008, provisional application No. 61/077,017, filed on Jun. 30, 2008.

(51) Int. Cl.
*A61B 19/00* (2006.01)

(52) U.S. Cl. .................... 606/130; 600/417; 600/429; 248/283.1

(58) Field of Classification Search ........... 83/821–829; 248/247.1, 276.1, 282.1, 283.1; 600/329, 600/417, 429; 606/54, 87, 96, 98, 130
See application file for complete search history.

(56) References Cited

U.S. PATENT DOCUMENTS

| | | | |
|---|---|---|---|
| 4,819,650 A | 4/1989 | Goldstein | |
| 4,841,979 A | 6/1989 | Dow et al. | |
| 5,048,529 A | 9/1991 | Blumenthal | |
| 5,070,879 A | 12/1991 | Herres | |
| 5,170,790 A | 12/1992 | Lacoste et al. | |
| 5,397,323 A * | 3/1995 | Taylor et al. | ................. 606/130 |
| 5,454,371 A | 10/1995 | Fenster et al. | |
| 5,842,473 A | 12/1998 | Fenster | |
| 5,931,786 A | 8/1999 | Whitmore, III et al. | |
| 5,964,707 A | 10/1999 | Fenster et al. | |
| 5,976,156 A * | 11/1999 | Taylor et al. | ................. 606/130 |
| 6,206,832 B1 | 3/2001 | Downey et al. | |
| 6,277,066 B1 | 8/2001 | Irwin | |
| 6,514,239 B2 | 2/2003 | Shimmura et al. | |
| 6,659,956 B2 | 12/2003 | Barzell et al. | |
| 6,788,018 B1 * | 9/2004 | Blumenkranz | ......... 318/568.11 |
| 7,066,889 B2 | 6/2006 | Taylor | |
| 7,189,246 B2 | 3/2007 | Otsuka et al. | |

(Continued)

FOREIGN PATENT DOCUMENTS

WO 2007106558 A2 9/2007

(Continued)

*Primary Examiner*—Terrell Mckinnon
*Assistant Examiner*—Daniel J Breslin
(74) *Attorney, Agent, or Firm*—Marsh Fischmann & Breyfogle LLP (57) ABSTRACT

Provided herein are devices and methods for supporting and positioning a tracking assembly for mounting variously configured medical devices for prostate imaging, biopsy, and other therapeutic applications. In one aspect, a support assembly provides multiple degrees of freedom for positioning a tracking assembly and mounted probe relative to a patient on a patient support structure such as an examination table or a gurney bed and/or maintaining a tracking assembly and mounted probe in a desired location throughout the rendering of imaging, biopsy, or other therapeutic procedures.

17 Claims, 10 Drawing Sheets

U.S. PATENT DOCUMENTS

| | | |
|---|---|---|
| 7,382,129 B2 | 6/2008 | Mills |
| 7,594,912 B2 * | 9/2009 | Cooper et al. .................. 606/1 |
| 7,762,825 B2 * | 7/2010 | Burbank et al. ............. 439/247 |
| 2008/0249403 A1 * | 10/2008 | Suri et al. ................... 600/437 |
| 2010/0204713 A1 * | 8/2010 | Ruiz Morales .............. 606/130 |

FOREIGN PATENT DOCUMENTS

WO 2007147232 A1 12/2007

* cited by examiner

SUPPORT ASSEMBLY FOR A TRACKING ASSEMBLY AND MOUNTED TRANSRECTAL ULTRASOUND PROBE

CROSS REFERENCE TO RELATED APPLICATIONS

This application claims the benefit of the filing date of U.S. Provisional Patent Application No. 61/077,017, entitled "Linear Positioning Apparatus," and having a filing date of Jun. 30, 2008 and also claims the benefit of the filing date of U.S. Provisional Patent Application No. 61/078,164, entitled "Tracking Device to Assist 3-D and 4-D Image Guidance," and having a filing date of Jul. 3, 2008, the entire contents of both of which are incorporated herein by reference.

FIELD OF INVENTION

The present invention is directed to systems and methods for positioning and locating a medical instrument relative to a patient. More particulary, the invention relates to an apparatus adapted to securely position a tracker assembly, which tracks 3-D locations of a supported medical device, relative to a patient.

BACKGROUND OF THE INVENTION

According to the National Cancer Institute, an estimated 234,000 new cases of prostate cancer will be diagnosed in the United States alone this year. Of these cases, more than 27,000 deaths due to prostate cancer are expected to occur this year. Following skin cancer, statistics show that prostate cancer is the most common cancer among American men.

Currently, medical professionals use a transrectal ultrasound-imaging device (TRUS) probe to acquire and guide prostate imaging and biopsy. The TRUS probe is the most widely accepted technique for prostate applications due to its simplicity, high specificity, and real time nature. In such an application, the TRUS probe may be inserted into the rectum of a patient to generate an image. Such images may be utilized to take one or more biopsies from a prostate location of interest and/or implant radioactive seeds at one or more desired locations in a brachy-therapy procedure. The TRUS probe may also be used in conjunction with other medical imaging applications, including cyrotherapy, photo-dynamic therapy, or a combination of these therapies and/or fusion-guided biopsies. With all of these applications, however, precise and repeatable TRUS probe placement and guidance is of utmost importance to achieve accurate imaging and rendering of the applicable therapy.

Prior art describes a number of methods and devices for assistance in guiding and placing the TRUS probe for imaging, biopsy, and therapy. Generally, these prior art devices utilize several mounting, stepping, and rotating devices for various commercially available TRUS probes. These tracking assemblies are typically stand-alone devices that utilize a combination of linkages and tracking mechanisms for monitoring the spatial position of a supported probe.

Such tracking assemblies are often not adapted for significant positional adjustment relative to the patient's body, as located on an examination table or a gurney bed. In order to "pre-fit" or "pre-position" such a tracking assembly to a patent, it has often been necessary to position the patient relative to the tracker assembly. In some instances, such limited tracker movement has impeded the accommodation of patients of varying heights and weights.

While extending the range of motion of the tracker assembly would apparently alleviate such pre-positioning difficulties, such expanded range of movement raises other difficulties. For instance, many tracking assemblies include a series of rotatively coupled armatures that allow extending and retracting the tracking assembly in one or more dimensions. To expand the range of movement of such devices, the length of the armatures would have to be increased. Considering the limited space often available in medical examination rooms, the armatures on any given tracking assembly would be prohibitively long to accommodate the movement often necessary to preposition the tracking assembly relative to a patient.

Beyond limited space constraints, increasing armature length to achieve necessary movement may introduce an unacceptable level of distortion into the spatial tracking of the tracking assembly.

SUMMARY OF THE INVENTION

The inventors of the present systems have recognized that solutions for pre-positioning a tracker assembly need not concentrate on the tracking assemblies themselves. Instead, such solutions may focus on a support and positioning device that is adapted to pre-position an entire tracking assembly relative to a patient's body. Accordingly, various aspects of the present invention provide a support assembly for vertically and horizontally positioning a tracking assembly relative to a patient's body. As discussed above, such tracking assemblies may be utilized to position medical probes or instruments relative to patient tissue of interest. Such medical devices may include, without limitation, a TRUS probe, a biopsy needle, therapeutic devices, medical imaging devices, etc.

The support assembly includes a base that supports a vertical tower. The vertical tower includes a linear positioning assembly. Interconnected to the linear positioning assembly is a horizontal linkage. The linear positioning assembly allows for positioning the horizontal linkage at a desired height. That is, the linear positioning assembly allows for positioning the linkage at a desired horizontal plane. The horizontal linkage includes at least first and second armatures that are connected by at least a first joint. A first end of the linkage interconnects to the linear positioning assembly and a second end of the linkage is a free end that provides a mounting surface for connection to a tracker assembly. The linkage allows for positioning its free distal end and a connected tracker within the horizontal plane. In this regard, after positioning a tracker at a desired height, the tracker may be advanced or retracted relative to a patient. Once a supported tracker is positioned in a desired location, the joint interconnecting the armatures of the linkage may be locked. In this regard, the supported tracker may be flexibly positioned at a desired location relative to a patient prior to performing a medical procedure on the patient.

Various refinements exist of the features noted in relation to the subject aspect of the present invention. Further features may also be incorporated in the subject aspect of the present invention as well. These refinements and additional features may exist individually or in any combination. For instance, the base element may be adapted for connecting the assembly to a patient support structure such as an examination table or a gurney bed. In another arrangement, the base element may be adapted for positioning on the floor. In such arrangement, the support assembly may be a freestanding unit.

The horizontal linkage may further incorporate multiple armatures. In such an arrangement, each of the armatures may be interconnected to adjacent armatures utilizing locking joints. In any arrangement, the horizontal linkage is operative to move between a retracted position and an extended position, thus allowing an operator to move a tracking assembly connected to the linkage relative to a patient's body.

The locking joints may be formed in an appropriate manner. Such joints may include single degree of freedom joints such as bushings, bearings, and hinges and/or multiple degree of freedom joints such as linear bearings, cylinders, rollers and ball/spherical joints. In one arrangement, single degree of freedom joints are utilized to maintain movement of the linkage within a common horizontal plane. In such an arrangement, two or more joints may permit movement about parallel axes. In any arrangement, it is desirable that the locking joints allow for fixedly positioning the distal end of the horizontal linkage. Such locking joints may be manually locked. Alternatively, the locking joints may be controllably actuated. For instance, the joints may be electromechanically, electromagnetically, hydraulically and/or pneumatically actuated. In one particular arrangement, a remote foot pedal may be utilized to actuate/lock the joints. In a further arrangement, each joint may be individually actuated.

In one arrangement, the linear positioning assembly includes a passive biasing device to assist in the vertical movement of the horizontal linkage and supported tracker assembly. In such an arrangement, the biasing device may include, without limitation, springs and/or compressed gas cylinders. Such passive devices may assist a user of the support assembly in manually adjusting the height of tracker device connected thereto.

In another arrangement, the linear positioning assembly may incorporate active biasing devices. Such active devices may include manually controlled devices such as cranks and pulleys as will as electromechanical actuators. In one arrangement, a linear actuator assembly is utilized. Such an assembly may be rodless or may utilize a threaded rod that may be controllably rotated relative to a threaded receptacle. Alternatively such actuators may be electromechanical, hydraulic or pneumatic. In such arrangements, the linear positioning assembly may be formed by a hydraulic/pneumatic cylinder. Further, it will be appreciated that the actuator could use a combination of these technologies. In one arrangement, the linear positioning assembly is controlled via remote switch to allow for hands-free vertical adjustment.

DETAILED DESCRIPTION

Reference will now be made to the accompanying drawings, which assist in illustrating the various pertinent features of the present disclosure. This disclosure primarily describes the present invention in conjunction with transrectal ultrasound imaging for prostate imaging. That said, one of ordinary skill in the art will appreciate that aspects of the present invention may be applicable to other medical imaging applications. For example, other embodiments of the present invention may be used in conjunction with brachy-therapy, cyrotherapy, photo-dynamic therapy, a combination of these therapies, fusion-guided biopsies, as well as other imaging and therapy applications. In this regard, the following description is presented for purposes of illustration and description only.

Figure 1:
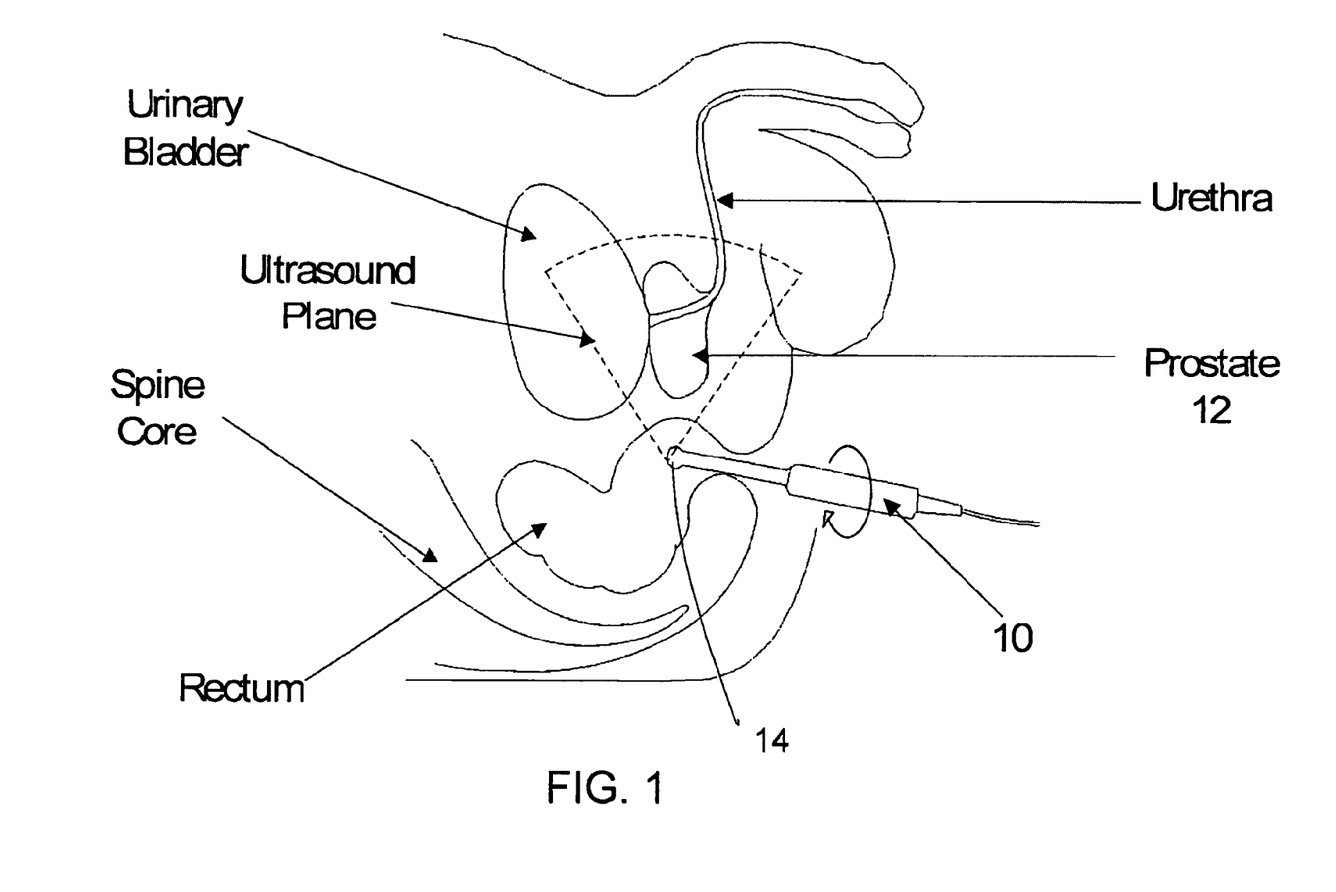
FIG. 1 shows a cross-sectional view of a transrectal ultrasound imaging probe as applied to perform prostate imaging, biopsy, or other therapy.
Figure 2:
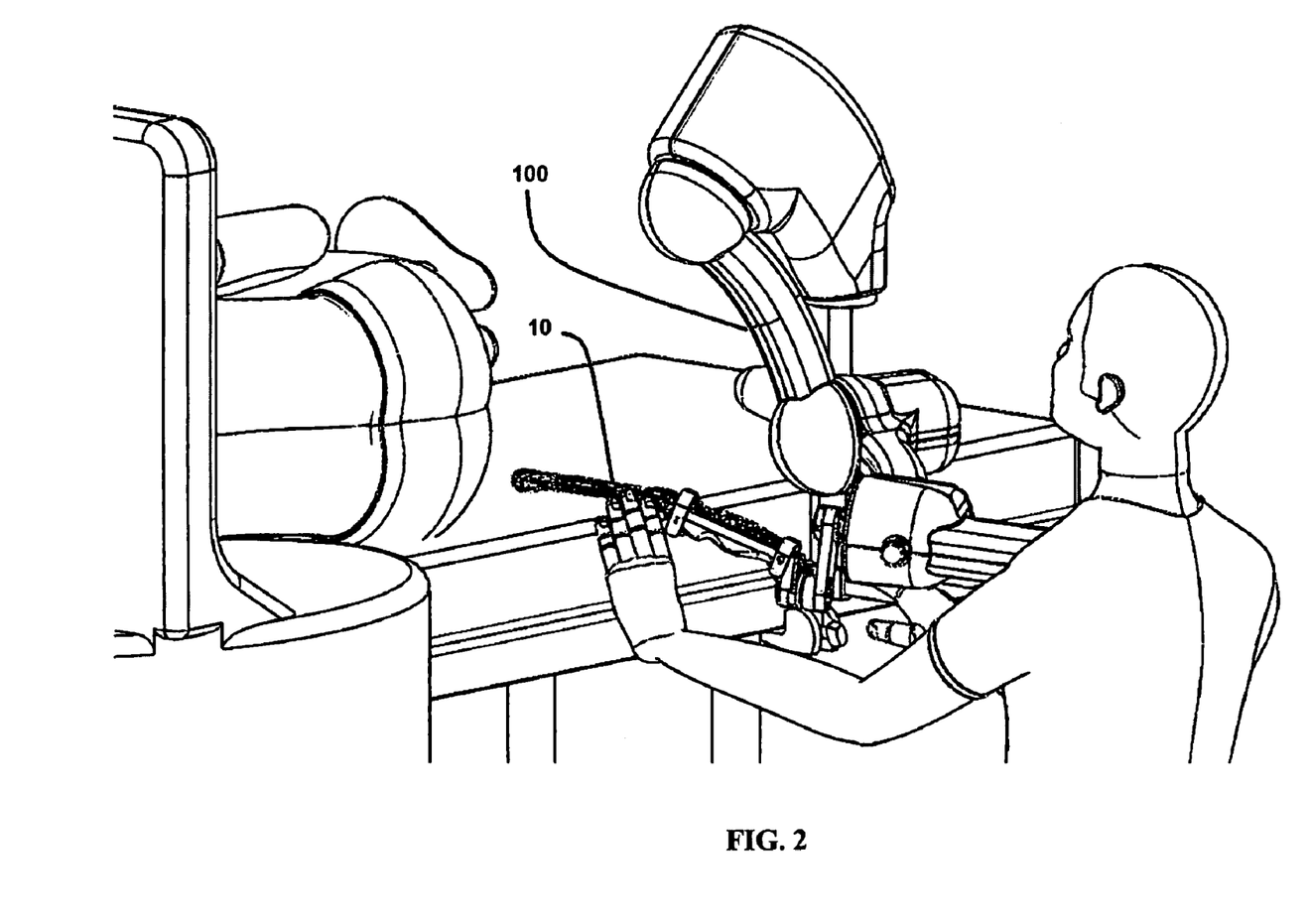
FIG. 2 illustrates use of a tracking assembly to position an ultrasound imaging prove to perform prostate imaging, biopsy, or other therapy.

As shown in FIGS. 1 and 2, one embodiment of the present invention may be adapted to fixedly position a tracking assembly for mounting a trans-rectal ultrasound (TRUS) probe or biopsy needle for medical imaging, biopsy, or other therapy. The support assembly of the present invention may interface with a tracking assembly such that a supported TRUS probe achieves target scanning of an area of interest within the prostate.

FIG. 1 illustrates a TRUS probe 10 being utilized to obtain a plurality of two-dimensional ultrasound images of the prostate 12. As shown, the probe 10 may be operative to automatically scan an area of interest. In such an arrangement, a user may rotate the acquisition end 14 of probe 10 over an area of interest. Accordingly, probe 10 may acquire a plurality of individual images while being rotated over the area of interest. In any arrangement, probe 10 may also include a biopsy gun (not shown) that may be attached to probe 10. Such a biopsy gun may include a spring driven needle that is operative to obtain a core from desired area within the prostate.

For imaging purposes, it is desirable to minimize relative movement between the probe 10 and the prostrate 12 (i.e., wobble or any other rotational movement of the probe about a fixed axis for image acquisition). It is also often desirable for probe 10 to remain fixed relative to the prostrate 12 during biopsy or other treatment procedures such that the desired tissue locations may be targeted accurately. To achieve such fixed positioning of probe 105 it is often desirable to interface the probe 10 with a tracking assembly 100, as shown in FIG. 2. Tracking assembly 100 maintains probe 10 in a fixed relative position to the prostate 12 as well as providing location information (e.g., frame of reference information) for use with an acquired image. In this regard, location outputs from tracking assembly 100 may be supplied to a computer and/or imaging device. Likewise, the output of the probe 10 may be provided to the computer and/or imaging device, and the computer and/or imaging device may utilize this information to produce an output (e.g., display) of imaged object (e.g., prostate).

The present invention may be used to position and fixably support various tracking assemblies of the type discussed above. One exemplary device is set forth in International Application Number PCT/CA2007/0001076, entitled Apparatus for Guiding a Medical Tool. Another is set forth in U.S. application Ser. No. 11/850,482, entitled Tracker Holder Assembly, the contents of which are fully incorporated herein by reference. Specifically, apparatuses are described that may be utilized to securely position such tracking devices and probe assemblies relative a patient support surface such as a gurney bed. Further, the apparatuses allow for movement of a supported tracking assembly in one or more degrees of freedom (DOF) so that a probe/medical device supported by the tracking assembly can be positioned in a desired position relative to a patient.

Figure 3:
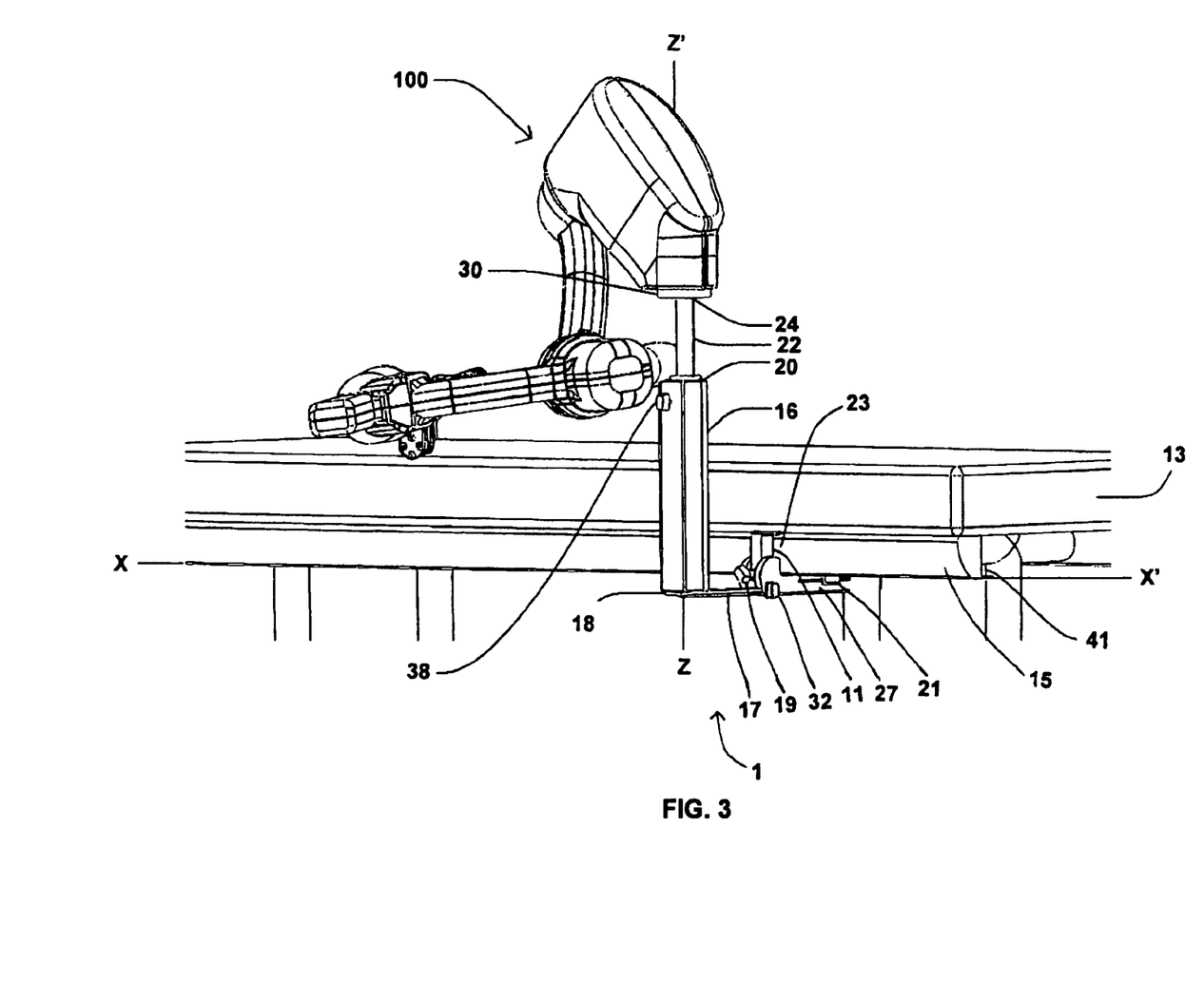
FIG. 3 illustrates a perspective view of one embodiment of a support assembly connected to a patient support structure and interconnected with a tracking assembly.

As previously discussed, oftentimes it is desirable to position a tracking assembly relative to a patient in a limited space environment such as a medical examination room, which may require a compact positioning/support assembly. The overall design and installation of one embodiment of such a compact support assembly 1, as attached to a gurney bed, is illustrated in FIG. 3. As shown, the support assembly 1 is securely clamped on to a gurney bed using a moveable jaw 11. A tracking assembly 100 is connected to the top of the support assembly. The support assembly 1 securely connects the tracking assembly 100 and supported probe to the gurney bed while allowing for selective positioning of the tracking assembly relative to the patient in one or more dimensions.

Specifically, the support assembly allows for selectively positioning the tracking assembly with multiple degrees of freedom (DOF) prior to initiating a medical procedure. As shown, and more fully discussed herein, the design allows for longitudinal motion along the length of the gurney bed, transverse motion relative to the width of the gurney bed (e.g., towards and away from a patient) as well as vertical up and down motion. For instance, it may be desirable to adjust the elevation of the supported tracking assembly along a vertical axis of the support assembly such that a probe supported by the tracking assembly is disposed relative to a centerline of a patient on a support surface. Once in such a position, the limited movement of the tracker assembly is typically sufficient for any further vertical adjustment relative to the patient. Finally, the support assembly allows for rotational motion of the tracking assembly about a vertical axis. In this regard, the support assembly 1 provides four degrees of freedom for selectively positioning the tracker assembly. Once an operator positions the support assembly in a desired location, the support assembly may be locked in place and a medical procedure may be performed.

Figure 4A:
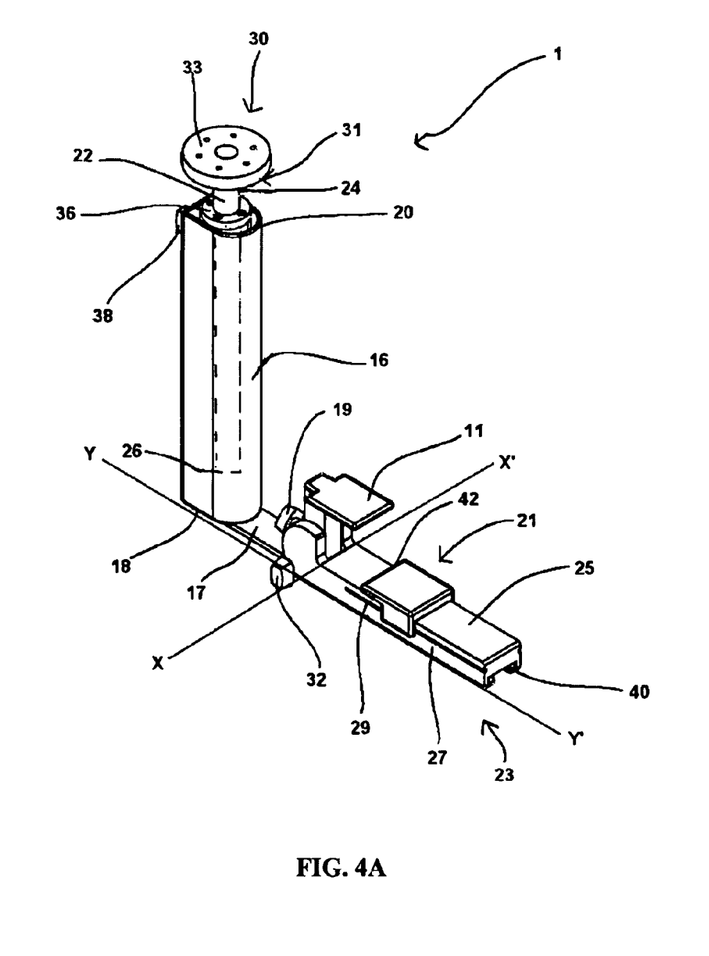
FIG. 4A illustrates a perspective view of the support assembly shown in FIG. 3 in a retracted position.
Figure 4B:
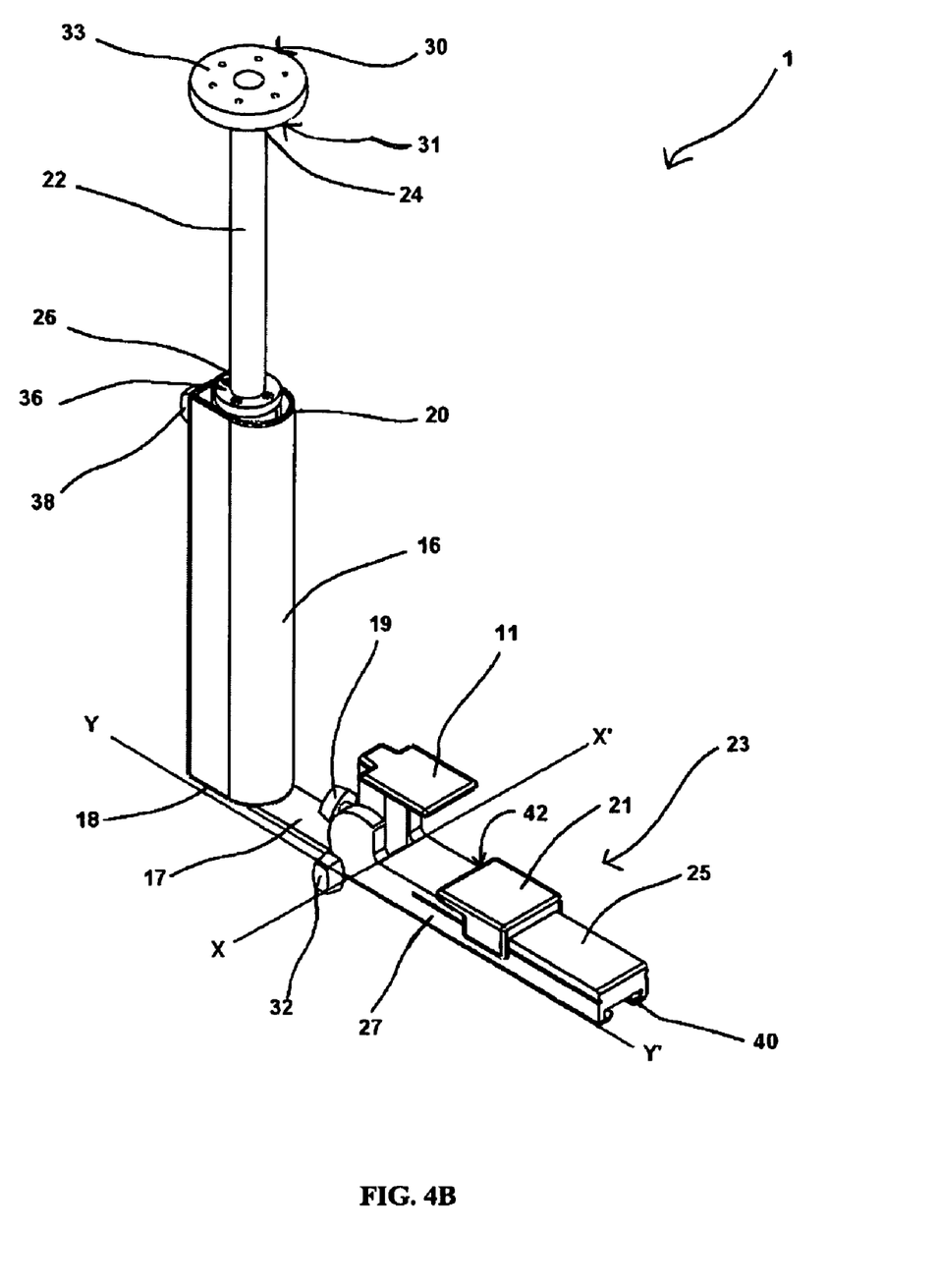
FIG. 4B illustrates a perspective view of the support assembly shown in FIG. 3 in an extended position.

In the embodiment illustrated in FIGS. 3 and 4A-B, support assembly 1 comprises a clamp assembly 23 for securely mounting support assembly 1 at a desired location along an edge 15 of the patient support structure 13, which defines a reference axis XX'. As shown, the clamp assembly 23 includes a body 27 having a top/base surface 25 and a movable jaw 11. In use, the top surface of the body is positioned below a frame of patient support structure 13 and the jaw 11 is disposed on an opposing side of the frame. Prior to advancing the jaw 11 relative to the base surface of the clamp assembly, an operator may move support assembly 1 along axis XX' to position the support assembly 1 relative to a patient. Once positioned at a desired location along the patient support structure 13, the jaw may be advanced relative to the base surface 25 of the clamp assembly 23 to compress the frame between the jaw 11 and base surface 25. The jaw 11 is adjusted vertically relative to the base surface 25 by releasing the mechanical friction lock 19. Once the frame of the patient support structure 13 has been compressed between the jaw 11 and the base surface 25, the friction lock 19 can be used to secure the clamping device at that particular position.

Safety lock 21 ensures that support assembly 1 remains fastened to patient support structure 13 as an operator moves support assembly 1 along axis XX'. As shown in FIGS. 4A-B, safety lock 21 is an L-shaped locking mechanism that comprises a tab 42 that extends toward jaw 11. Tab 42 is adapted to slip fit with the underside lip 41 (FIG. 3) of the frame of the patient support structure 13. In addition, safety lock 21 is slidably engaged within a slot 29 such that safety lock 21 may be adjusted to engage patient support structures of varying frame widths. In this embodiment, safety lock 21 ensures that support assembly 1 remains engaged with the underside lip 41 of the patient support structure 13 when the operator loosens the clamp assembly 23 to move support assembly 1 along axis XX'.

Once the frame is compressed between the jaw 11 and base surface 25 of the clamp assembly 23, the support assembly 1 may be secured via a mechanical friction lock 19. In the present embodiment, the clamp locking mechanism is a mechanical lock comprising a set screw (not shown) that extends though a threaded aperture in the base member of the clamp assembly 23 to engage the jaw 11. This locks the jaw relative to the clamp body 27. However, it will be appreciated that in other embodiments, the mechanical friction lock 19 may be manual, electromechanical, electromagnetic, hydraulic, pneumatic, or any combination of these technologies.

As shown in greater detail in FIGS. 4A-B, support assembly 1 further comprises a hollow sleeve member 16 having a first end 18 and a second end 20. The first end 18 of sleeve member 16 may be slidably interconnected to clamp assembly 23 via a bearing (not shown) that interfaces with a sliding member 17. As shown, the sliding member 17 is formed of a beam/strap having a substantially rectangular cross-sectional shape. This strap is received in a corresponding channel 40 formed in the bottom of the body 27 of the clamp assembly 23. An operator may position sliding member 17 between a fully retracted position and fully extended position along a reference axis YY', which is perpendicular to reference axis XX'. An operator may then engage slide member locking mechanism 32 to secure sliding member 17, and thus sleeve member 16, at a desired position relative to the width of the patient support structure 13 along axis YY'. In the present embodiment, the slide member lock mechanism 32 is a set screw (not shown) that extends through a threaded aperture in the body 27 of the clamp assembly 23. When advanced, a distal tip of the set screw extends into the channel 40 and engages the sliding member 17. One of ordinary skill in the art will understand that slide member locking mechanism 32 may, in other embodiments, be manual, electromechanical, electromagnetic, hydraulic, pneumatic, or any combination of these technologies.

To position an attached tracking assembly vertically relative to a patient, a shaft 22 having a top end 24 and a bottom end 26 may be disposed within sleeve member 16. When disposed within sleeve member 16, shaft 22 defines a reference axis ZZ' (FIG. 3) that is transverse to both reference axes XX' and YY' (FIGS. 4A-B). In use, the sleeve member 16 is typically oriented vertically such that reference axis ZZ' defines a vertical reference axis. The shaft 22 is linearly coupled to sleeve member 16 via a sleeve bearing (not shown) that facilitates linear movement of shaft 22 along reference axis ZZ' between a fully retracted position (see FIG. 4A) and a fully extended position (see FIG. 4B).

In the fully retracted position, shown in FIG. 4A, the top end 24 of the shaft 22 extends minimally above the second end 20 of the sleeve member 16. When extended, the top end 24 of the shaft 22 may extend significantly above the top end of the sleeve member. In the illustrated embodiment, the shaft 22 is operative to move at least five inches. Those of ordinary skill in the art will readily understand that the linear movement of shaft 22 along reference axis ZZ' may be actuated manually, electromechanically, hydraulically, pneumatically, or through any combination of these technologies. In the present embodiment, the shaft 22 is spring biased. A compression spring (not shown) may be disposed within sleeve member 16 such that the spring is operative to exert a force between the shaft 22 and the sleeve member 16. In this configuration, the spring assists an operator of the support assembly 1 in manually adjusting the height of mounted tracking assembly 100. It will be appreciated that the spring may comprise a mechanical coil or helical compression spring or it could be a gas cylinder.

To rotatively position an attached tracking assembly about reference axis ZZ', shaft 22 may be rotatively coupled to sleeve member 16 via a surface bearing 36. The top end 24 of shaft 22 may be fixably coupled to the tracking assembly via a mounting surface 30. Specifically, a bottom side 31 of mounting surface 30 may be fixably coupled to the top end 24 of shaft 22, while a top side 33 of mounting surface 30 may be fixably coupled to tracking assembly 100 (FIG. 3) such that tracking assembly 100 and shaft 22 may rotate together about reference axis ZZ'. A shaft locking mechanism 38 may secure shaft 22 and tracking assembly 100 at a desired vertical and angular position. As discussed above, one of ordinary skill in the art will readily understand that the shaft locking mechanism 38 may be manual, electromagnetic, electromechanical, hydraulic, pneumatic, or a combination of these technologies.

In an alternative embodiment, tracking assembly 100 may be rotatively coupled to mounting surface 30 via a surface bearing such that tracking assembly 100 rotates independently of, and about, shaft 22.

FIGS. 5 through 8A-B illustrate the overall design of another embodiment of a support assembly for positioning the tracking assembly 100 relative to a patient. In the embodiment shown, a support assembly 50 may be positioned on the floor or any other stable surface located next to patient support structure 13. Further, the support assembly 50 allows for achieving precise linear positioning within multiple degrees of freedom prior to initiating a medical procedure. As more fully discussed below, support assembly 50 comprises a vertical tower assembly that, with the aid of a custom linear actuator assembly, provides vertical positioning relative to the height of the patient support structure and/or the centerline of a patient. This embodiment also incorporates a robotic horizontal linkage that interfaces the supported tracking assembly and the vertical tower assembly and allows for selectively positioning the tracking assembly within the horizontal plane. In this regard, the horizontal linkage comprises two armatures that are rotatively coupled through two electromagnetic locking joints. By engaging and disengaging the electromagnetic clutches associated with the locking joints, the horizontal linkage provides rotational motion about one or both of the electromagnetic locking joints. This allows the horizontal linkage to advance and retract in the horizontal plane, providing for positioning of the supported tracking assembly and probe with a great deal of motion within an additional degree of freedom. Once an operator positions the support assembly in a desired location and locks the horizontal linkage, a supported tracker assembly is securely positioned and a medical procedure may be performed.

The embodiment shown in FIGS. 5 through 8A-B may also provide for operator controls (e.g., push buttons and limit switches) to control the overall length of travel in both the vertical and horizontal planes to ensure operational safety and ease of use. To further ensure safety and ease of use, as well as to provide a compact and neat packaging design, the components of the support assembly 50 are configured to route and manage several wires or cables, including, for example, power cords for the tracking assembly, an associated computer and/or monitor, and network cabling.

Figure 5:
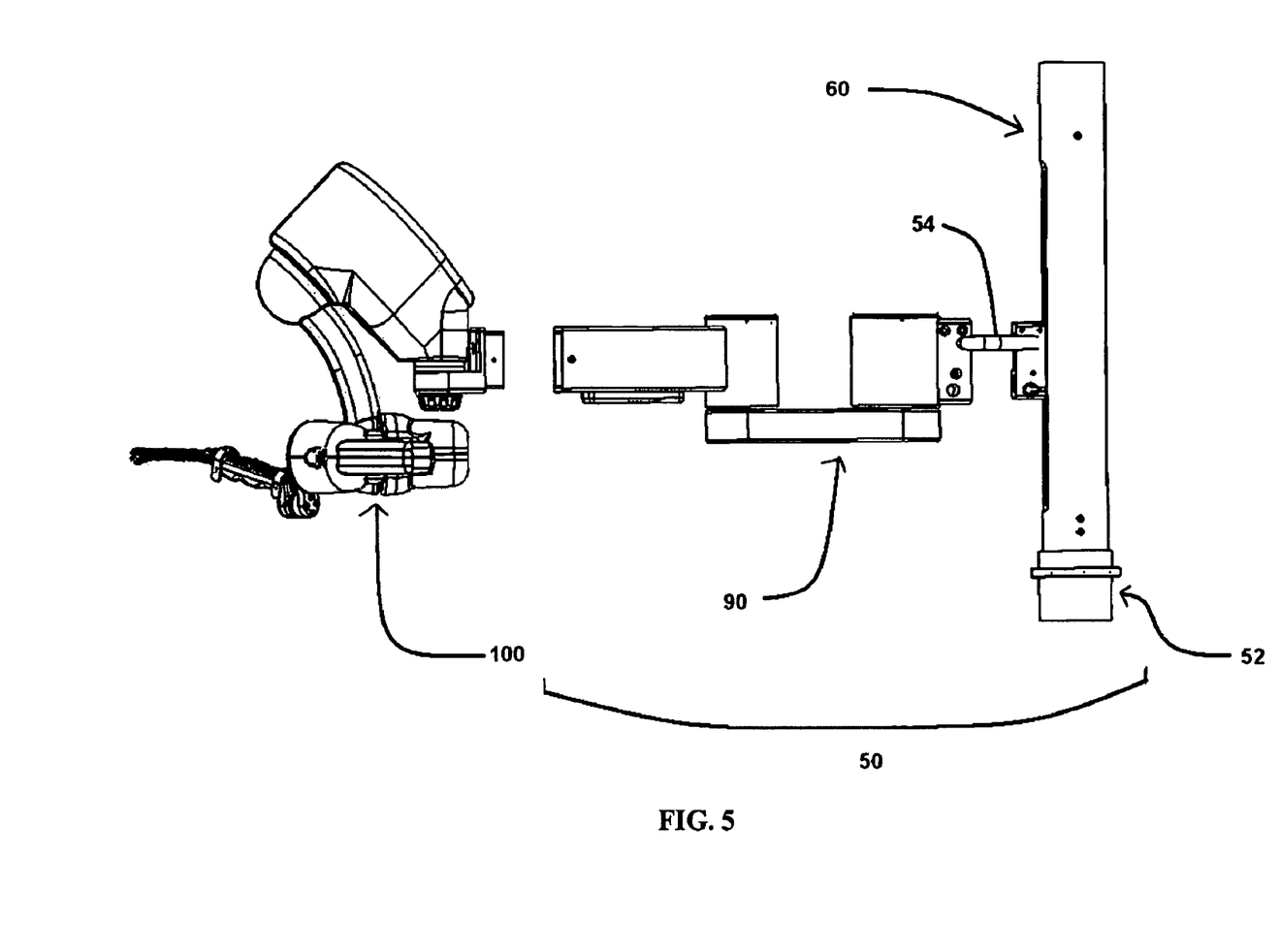
FIG. 5 illustrates a side plan view of another embodiment of a support assembly adapted to be positioned on the floor.

In the embodiment shown in FIGS. 5 through 8A-B, support assembly 50 comprises a base element 52, a vertical tower assembly 60, and a horizontal linkage 90 adapted to fixably support tracking assembly 100, as shown in FIG. 5. Base element 52 and vertical tower assembly 60 are moveably coupled to a horizontal linkage 90 via a linking cuff 54.

Figure 6:
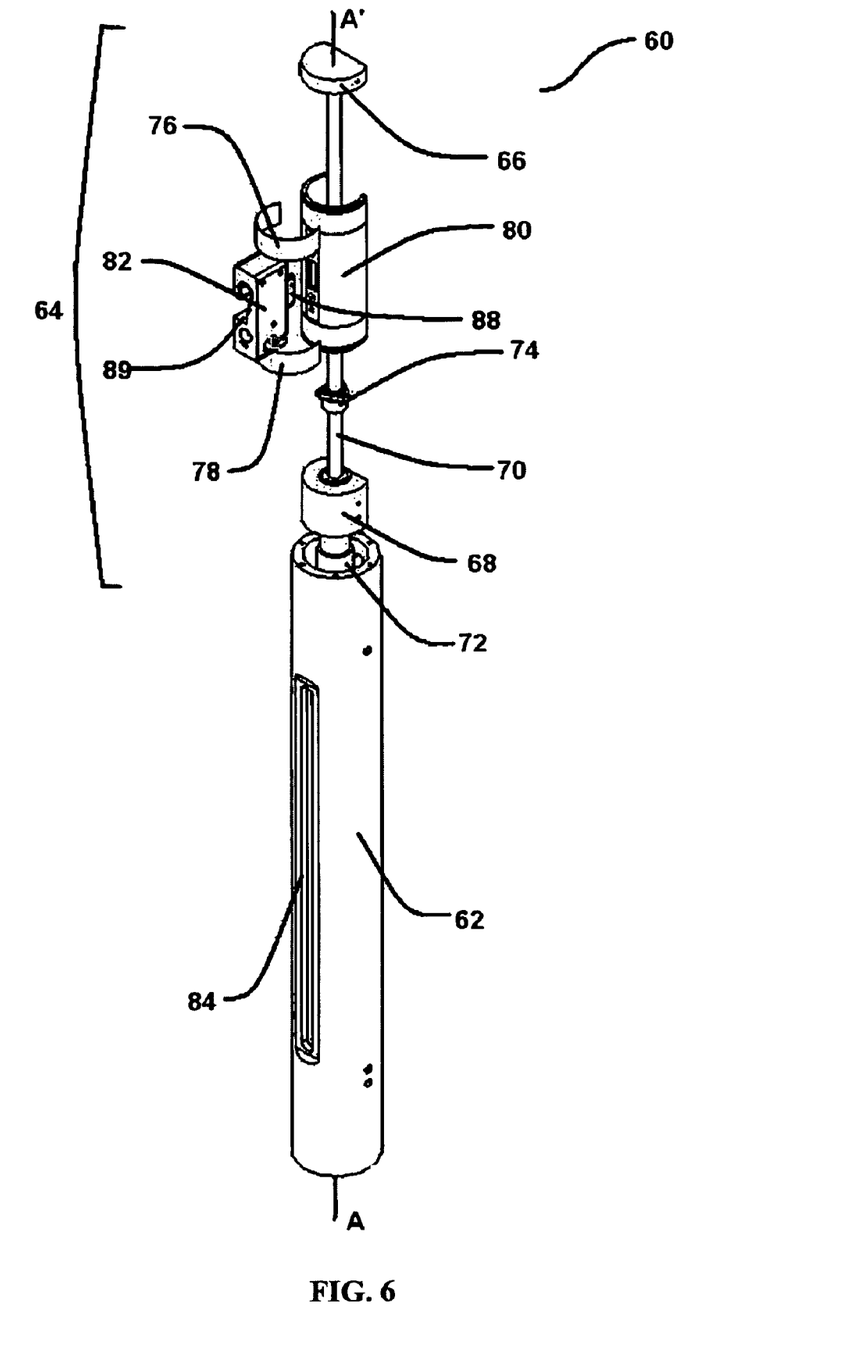
FIG. 6 illustrates an exploded view of a vertical tower assembly for use with the support assembly shown in FIG. 5.

FIG. 6 illustrates an exploded view of vertical tower assembly 60. In this embodiment, vertical tower assembly 60 comprises a vertical sleeve member 62 having a vertical slot 84, and a linear actuator assembly 64 is mounted within vertical sleeve member 62 via a top mounting block 66 and a bottom mounting block 68. The vertical slot 84 is configured to allow access for the linear actuator assembly 64 to fixably connect with the horizontal linkage 90. When connected with the linear actuator assembly 64, horizontal linkage 90 moves upward and downward vertically in conjunction with the movement of the linear actuator assembly, as detailed below.

Linear actuator assembly 64 comprises a threaded shaft 70, an actuator 72, a threaded receptacle 74, an inner sleeve member 80, two low friction sleeve bearings 76, 78, and a vertical sleeve connecting block 82. Specifically, threaded shaft 70 is rotatively suspended between top mounting block 66 and bottom mounting block 68, defining a reference axis AA'. Actuator 72 is mounted within vertical sleeve member 62 to threaded shaft 70 and is adapted to rotate threaded shaft 70 relative to threaded receptacle 74. Those of ordinary skill in the art will readily understand that actuator 72 may be an electromechanical device, such as a servo motor, or it may be manual, hydraulic, pneumatic, or a combination of these technologies. Those skilled in the art will also recognize that threaded receptacle 74 may be a nut or any other internally threaded fastener known in the art.

Threaded receptacle 74 may be coupled to inner sleeve member 80 such that when threaded shaft 70 rotates, threaded receptacle 74 and inner sleeve member 80 move between a bottom position and a top position along reference axis AA'. Low friction sleeve bearings 76, 78 may attach to inner sleeve member 80 to facilitate smooth linear motion between inner sleeve member 80 and vertical sleeve member 62. Exemplary low friction sleeve bearings may be purchased from Igus® Inc., or any other suitable bearing manufacturer as is generally known in the art.

Limit switches (not shown) are located at both ends of the linear actuator assembly 64 at the top mounting block 66 and the bottom mounting block 68. The limit switches are generally maintained in an open state. As the inner sleeve member 80 reaches its top or bottom positions, it contacts the limit switches, cutting power to the actuator 72 and providing a smooth and safe stop.

As shown in FIG. 5, a linking cuff 54 interconnects vertical tower assembly 60 with horizontal linkage 90. As discussed in greater detail below, this embodiment of horizontal linkage 90 comprises two armatures and two electromagnetic locking joints. Rotating the armatures about one or both joints allows for the compact retraction and significant extension of the armature.

Through linking cuff 54, vertical tower assembly 60 is able to move horizontal linkage 90 vertically relative to reference axis AA', which, in turn, also moves a supported tracking assembly 100 vertically in relation to reference axis AA'. In greater detail, a proximal flange 88 of vertical sleeve connecting block 82 fixably connects to inner sleeve member 80 through vertical slot 84 within vertical sleeve member 62. At least one distal aperture 89 of vertical sleeve connecting block 82 mates with linking cuff 54, which in turn connects to horizontal linkage 90.

While the vertical tower assembly 60 allows for vertically positioning the tracking assembly 100 to a desired height (i.e., horizontal plane), the horizontal linkage 90 allows for selectively positioning the tracker assembly 100 within the horizontal plane. In this regard, the linkage 90 includes various rotatively coupled armatures that allow at least for significant in-plane movement of the distal end of the horizontal linkage, as will be discussed in greater detail below.

Figure 7:
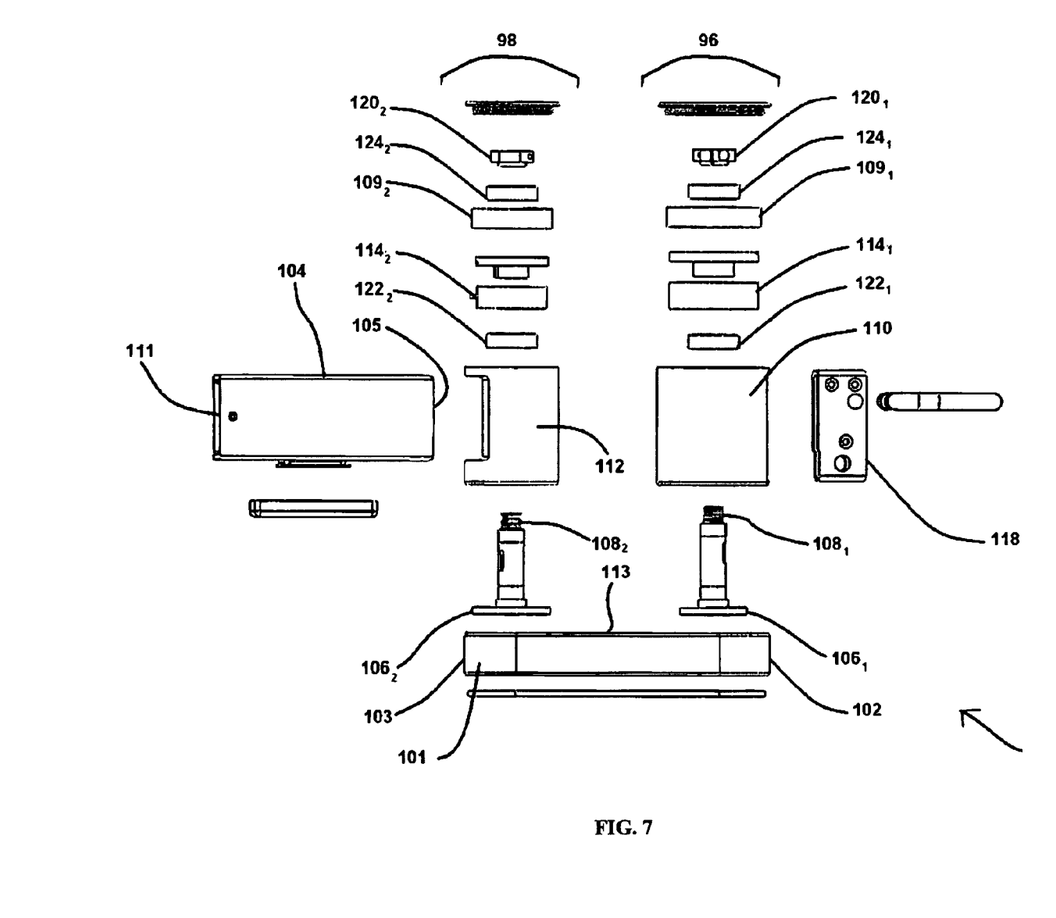
FIG. 7 illustrates an exploded view of a horizontal linkage for use with the support assembly shown in FIG. 5

FIG. 7 illustrates an exploded view of horizontal linkage 90. Horizontal linkage 90 comprises a first armature 101 having a proximal end 102 and a distal end 103 and a second armature 104 having a proximal end 105 and a distal end 111. It will be appreciated that the distal end 111 of second armature 104 also forms a free distal end of horizontal linkage 90.

Figure 8A:
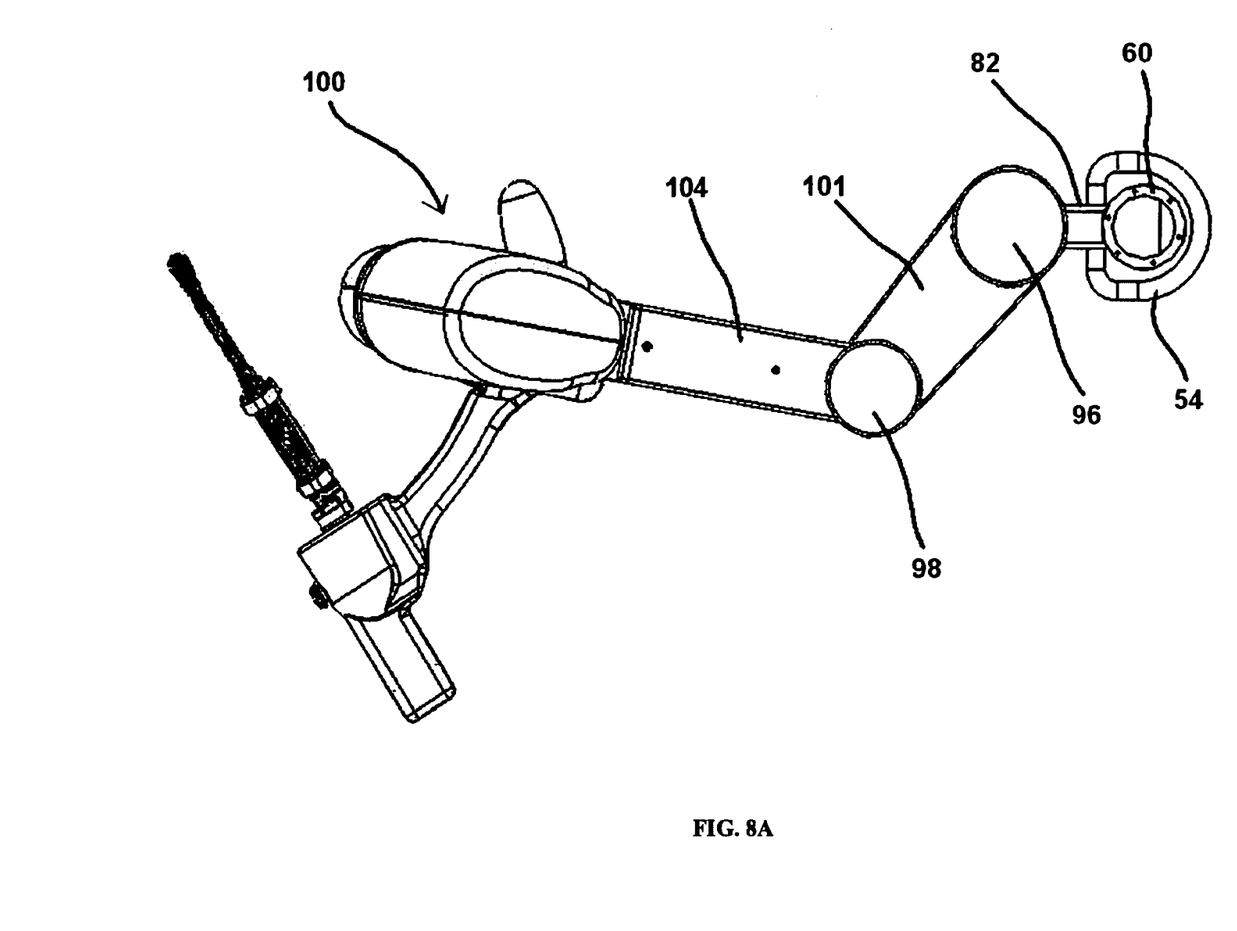
FIG. 8A illustrates a top plan view of the support assembly shown in FIG. 5 in an extended position.
Figure 8B:
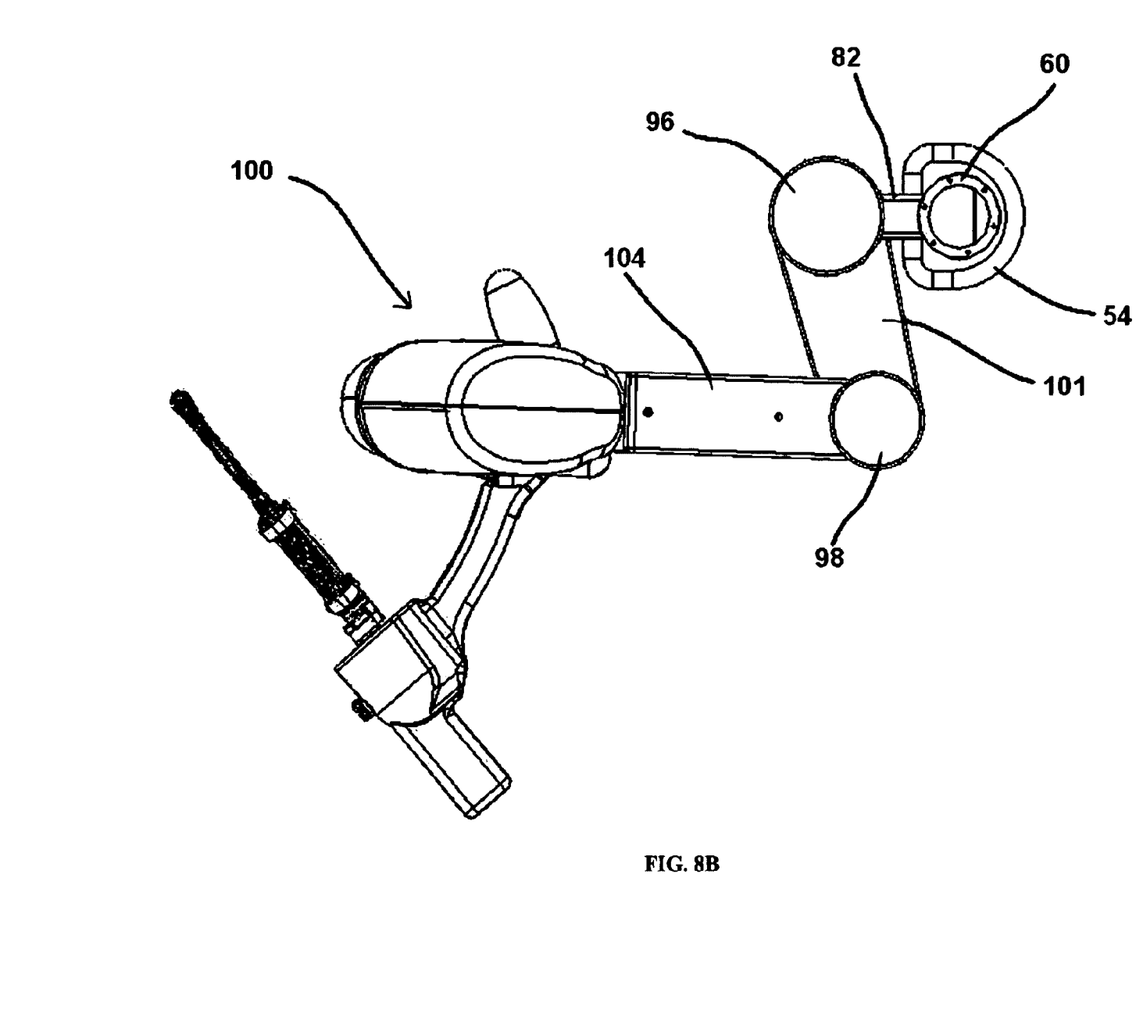
FIG. 8B illustrates a top plan view of the support assembly shown in FIG. 5 in a retracted position.

FIGS. 8A-B illustrate that one embodiment of horizontal linkage 90 further comprises two electromagnetic locking joints 96, 98, about which first armature 101 and second armature 104 may be rotationally adjusted to provide an expanded motion within the horizontal plane. For instance, first electromagnetic locking joint 96 may be rotated to position the distal end 111 of the second armature 104 such that it is disposed at least partially behind or beside the vertical tower assembly 60 in a collapsed position (FIG. 8B). It will be appreciated that moving the first armature 101 and second armature 104 between expanded and retracted positions, as shown in FIGS. 8A-B, respectively, gives horizontal linkage 90 a significant range of motion within the horizontal plane while taking advantage of a compact design of limited armature length The electromagnetic locking joints 96, 98 each comprise a joint shaft $106_{1\text{-}2}$ having a threaded top end $108_{1\text{-}2}$, respectively. Joint shaft $106_1$ is fixably coupled with proximal end 102 of a top surface 113 of first armature 101, and joint shaft 1062 is fixably coupled with distal end 103 of top surface 113 of first armature 101. At each electromagnetic locking joint 96, 98, an electromagnetic clutch $114_{1\text{-}2}$ and at least two surface bearings $122_{1\text{-}2}$, $124_{1\text{-}2}$ may be positioned about joint shafts $106_{1\text{-}2}$, respectively Surface bearing $122_{1\text{-}2}$ may be press fit into machined housings 110, 112, while bearing spacers $109_{1\text{-}2}$ may be fixably positioned between surface bearings $124_{1\text{-}2}$ and housings 110, 112. Further, electromagnetic clutches $114_{1\text{-}2}$ may be affixed to housings 110, 112, such that they selectively engage and disengage joint shafts $106_{1\text{-}2}$ to control the rotational motion of first armature 101 and second armature 104 about electromagnetic locking joints 96, 98, respectively. Finally, retaining nuts $120_{1\text{-}2}$ may be tightened about the threaded top ends $108_{1\text{-}2}$ of joint shafts $106_{1\text{-}2}$ in order to compress housings 110, 112 against top surface 113 of first armature 101 such that each component of electromagnetic locking joints 96, 98 is contained within housings 110, 112.

When electromagnetic clutches $114_{1\text{-}2}$ are actuated, they engage joint shafts $106_{1\text{-}2}$ such that the free distal end 111 of horizontal linkage 90 is locked in place to maintain the supported tracking assembly 100 in a desired position. One or more operator control devices such as push buttons (not shown) may be mounted alongside the keyboard of a control computer (not shown) that is externally connected to the tracking assembly 100 to provide the electrical/electronic controls for the linear actuator and electromagnetic locking joints/clutches. It will be appreciated that these devices may also be actuated through other types of remote switches such as, for example, a foot pedal (not shown).

Housing 112 is configured to fixably couple with second armature 104. One of ordinary skill in the art will readily understand that this, as well as all of the fixed couplings discussed above, may be accomplished via threaded fasteners, rivets, pins, welding, a press fit, an adhesive, or any other method generally known in the art. Moreover, distal end 111 of second armature 104 may be adapted to support tracking assembly 100, as shown in FIG. 5.

To assist with cable management and routing, the components of vertical tower assembly 60 and horizontal linkage 90 may be configured to allow at least one cable to pass internally through vertical tower assembly 60 and horizontal linkage 90. In greater detail, vertical sleeve member 63, top and bottom mounting blocks 66, 68, inner sleeve member 80, low friction sleeve bearings 76, 78, vertical sleeve connecting block 82, horizontal linkage connecting block 118, first armature 101, second armature 104, and joint shafts $106_{1\text{-}2}$ may be formed such that they allow for the passage of cabling.

While FIGS. 5 through 8A-B illustrate an embodiment of support assembly 50 adapted to be positioned on the floor or any other stable surface located near patient support structure 13, one of ordinary skill in the art will readily understand that support assembly 50 may be configured to attached directly to patient support structure 13 via a clamping device or another suitable method of attachment.

The foregoing description of the present invention has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. The embodiments described hereinabove are farther intended to explain best modes known of practicing the invention and to enable others skilled in the art to utilize the invention in similar or other embodiments and with various modifications required by the particular application(s) or use(s) of the present invention. It is intended that the appended claims be construed to include alternative embodiments to the extent permitted by the prior art.

What is claimed is:

1. A support assembly for fixably positioning a tracking assembly for use in locating and positioning a medical device, comprising:
   a base element;
   a vertical tower connected to the base element, the vertical tower including a linear actuator assembly for selective vertical positioning; and
   a horizontal linkage having a first end and a free distal end, wherein the first end is connected to the linear actuator assembly of the vertical tower and the free distal end provides a mount for connection to a tracking assembly, the horizontal linkage comprising:
   a first armature;
   a second armature; and
   an electromagnetic locking joint connecting the first and second armatures, wherein activating the electromagnetic locking joint locks the joint and fixedly positions the free distal end of the horizontal linkage.

2. The support assembly of claim 1, wherein the horizontal linkage further comprises:
   at least two electromagnetic locking joints.

3. The support assembly of claim 2, wherein a first electromagnetic locking joint connects the first end of the horizontal linkage to the linear actuator assembly of the vertical tower and a second horizontal locking joint connects the first and second armatures.

4. The support assembly of claim 2, wherein the first and second electromagnetic locking joints permit rotation about first and second parallel axes.

5. The support assembly of claim 2, wherein the first and second electromagnetic locking joints are individually actuable.

6. The support assembly of claim 1, wherein the base element is adapted for connection to a patient support structure.

7. The support assembly of claim 1, wherein the base element is adapted for positioning on the floor.

8. The support assembly of claim 1, wherein the linear actuator assembly comprises:
   a threaded shaft; and
   an actuator connected to the threaded shaft, wherein the actuator is adapted to rotate the threaded shaft relative to a threaded receptacle.

9. The support assembly of claim 1, wherein the linear actuator assembly comprises a cylinder.

10. The support assembly of claim 1, wherein the linear actuator assembly is electromechanical.

11. The support assembly of claim 1, wherein the vertical tower comprises:
    a vertical sleeve member that at least partially houses the linear actuator assembly.

12. The support assembly of claim 11, wherein the linear actuator assembly is selected from a group comprising at least one of: manual, hydraulic, electromechanical, and pneumatic.

13. The support assembly of claim 11, further comprising:
    at least one low friction sleeve bearing coupled to an inner sleeve member; and
    a vertical sleeve connecting block for interconnecting the vertical tower and the horizontal linkage, wherein the vertical sleeve connecting block extends through a vertical slot in the vertical sleeve member.

14. The support assembly of claim 13, wherein the vertical sleeve member, the at least two mounting blocks, the inner sleeve member, and the low friction sleeve bearing include aligned recesses for routing a cable through the vertical sleeve assembly.

15. The support assembly of claim 1, further comprising a remote switch for controlling the linear actuator assembly.

16. The support assembly of claim 1, wherein the electromagnetic locking joint comprises:
    a joint shaft, wherein the joint shaft is fixably connected to the first armature of the horizontal linkage;
    a housing fixedly connected to the second armature of the horizontal linkage, the housing sized to receive the joint shaft;
    an electromagnetic clutch fixably connected to the housing, wherein the electromagnetic clutch is configured to engage the joint shaft at a desired angular position.

17. The support assembly of claim 16, wherein the housing is rotatively coupled to the joint shaft through at least two surface bearings.

\* \* \* \* \*

UNITED STATES PATENT AND TRADEMARK OFFICE
CERTIFICATE OF CORRECTION

| | | |
|---|---|---|
| PATENT NO. | : 7,875,039 B2 | Page 1 of 1 |
| APPLICATION NO. | : 12/207708 | |
| DATED | : January 25, 2011 | |
| INVENTOR(S) | : Amit Vohra and Jasjit S. Suri | |

It is certified that error appears in the above-identified patent and that said Letters Patent is hereby corrected as shown below:

<u>Column 1</u>
Line 21, delete "particulary" and insert therefor --particularly--.

<u>Column 3</u>
Line 33, delete "will" and insert therefor --well--.

Signed and Sealed this
Eighth Day of March, 2011

David J. Kappos
*Director of the United States Patent and Trademark Office*